United States Patent
Kumar et al.

(10) Patent No.: US 6,709,853 B2
(45) Date of Patent: Mar. 23, 2004

(54) PROCESS FOR THE PREPARATION OF CELL BEADS BOD SENSOR USEFUL FOR INSTANT BOD ESTIMATION

(75) Inventors: Rita Kumar, Delhi (IN); Shikha Rastogi, Delhi (IN); Alka Sharma, Delhi (IN); Tushya Kumar Saxena, New Delhi (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 09/825,571

(22) Filed: Apr. 3, 2001

(65) Prior Publication Data

US 2003/0036186 A1 Feb. 20, 2003

(51) Int. Cl.[7] ............ C12N 1/20; C12N 1/02; C12N 1/04; C12N 11/02; C12P 39/00
(52) U.S. Cl. ............ 435/252.1; 435/41; 435/42; 435/162; 435/170; 435/177; 435/252.4; 435/253.3; 435/260; 435/261
(58) Field of Search ............ 435/41, 42, 162, 435/170, 177, 252.1, 252.4, 253.3, 260, 261

(56) References Cited

FOREIGN PATENT DOCUMENTS

| DE | 19939236 | * | 2/2001 |
| GB | 2360788 | * | 10/2001 |

* cited by examiner

Primary Examiner—Christopher R. Tate
Assistant Examiner—Kailash C. Srivastava
(74) Attorney, Agent, or Firm—John P. White; Cooper & Dunham LLP

(57) ABSTRACT

Immobilized cell beads incorporating formulated microbial consortium comprising a synergistic mixture of the following bacterial strains namely, *Enterobacter sakazaki*, *Pseudomonas aeruginosa* and *Aeromonas sobria* selected from the following isolated bacterial strains namely, *Yersinia enterocolitica, Aeromonas sobria, Klebsiella pneumoniae, Serratia liquefaciens, Enterobacter sakazaki, Citrobacter amalonaticus, Pseudomonas fluorescens, Pseudomonas aeruginosa, Enterobacter cloaca, Acinetobacter calcoaceticus* are prepared, the formulated microbial consortium is immobilized in an appropriate immobilizing agent resulting in the formation of beads and the beads are used for instant BOD estimation using an electronic device and the formulated cell beads are reusable and are capable of assimilating most of the organic matter present in varied industrial effluents.

19 Claims, No Drawings

US 6,709,853 B2

PROCESS FOR THE PREPARATION OF CELL BEADS BOD SENSOR USEFUL FOR INSTANT BOD ESTIMATION

FIELD OF THE INVENTION

The present invention relates to a process for the preparation of cell beads BOD sensor useful for instant BOD estimation. The cell beads comprise of a formulated, synergistic, immobilized microbial consortium.

DESCRIPTION OF THE PRIOR ART

The problem of water pollution is increasing day by day with industrial development and urbanization. Many toxic and recalcitrant chemical compounds are being released in increasing amounts in the aquatic environment without proper treatment. The multitude of industries are by far the largest pollution creating units, whose discharges require a great degree of detoxification before they are released into the aquatic environment.

Before diverting the industrial effluents for treatment, their monitoring is crucial. Monitoring is an essential tool for waste-water management, for it details the ambient or background pollution level. Till date, classical chemical or spectrophotometric methods, requiring long reaction time and complicated procedures are used for monitoring of parameters/compounds of environmental interest such as Biochemical Oxygen Demand (BOD), heavy metals, pesticides, phenols, etc.

Amongst all these, BOD is a key parameter in the monitoring of water quality and treatment. BOD is a measure of the oxygen demand in a sample as a result of its organic content. BOD plays a very crucial role in assessing the pollutional strength of waste-waters, as high BOD means high organic content which further implies an increased consumption of oxygen to decompose these organics. BOD test is still carried out by the conventional method, which is very tedious and time consuming. The control of waste-water plants is difficult or even impossible using the classical determination method for BOD because of its high time consumption of five days.

Thus, there arises a need for determining the BOD values within minutes, which is possible only by using rapid BOD measuring devices. Sensors, which are devices that transduce a selective biochemical response into an electrical signal, can offer practical alternatives in environmental monitoring in terms of convenience, ability to reduce the reaction time and test system's complexity to a minimum and suitability for on-line applications.

For environmental monitoring, microbial biosensors are extensively used as compared to enzyme sensors. This is so because cell based sensors show a high degree of stability and are able to perform complex reaction sequences. Moreover, microorganisms employed in microbial biosensors are relatively easy to maintain in pure cultures, grow up and harvest at low cost, circumventing the costly extraction and purification procedures prior to use as biocatalysts as in the case of enzyme based sensors. In addition, BOD sensing by rapid devices cannot be achieved using enzyme-based sensors as BOD test is a sequence of complex reactions requiring an array of enzymes which are difficult to assemble at a time on a support. As evident from the literature, one report on whole cell based sensor for BOD estimation is available using single pure culture of microorganism (Su et al. 1986). The drawback of such developed cell beads sensor using single pure culture is that a single microbe is unable to assimilate all the organic matter present in the test sample; from either a single or a wide range of industries.

For solving the aforementioned problems, the applicants have realized that there exists a need to provide a process for the preparation of a defined synergistic microbial consortium immobilized in a suitable support i.e., agarose, useful for instant BOD estimation.

To overcome these problems, a number of bacterial strains have been used for the preparation of cell beads sensor individually as well as in combination. When the cell beads sensor using, single microorganism was used for instant BOD estimation they did not serve the said purpose. On the other hand, if the cell beads are prepared using combinations of microorganisms having synergistic effect and used for instant BOD estimation, it may yield reproducible and reliable results. Besides, the immobilization support also plays a crucial role in determining the response time and sensitivity of the sensor. Greater is the shelf life, stability and viability of the immobilized biocatalyst, better is the response.

In the present invention, cell beads sensor has been developed by immobilizing the formulated microbial consortium on a suitable support i.e., agarose under a hydrophobic condition, useful for instant BOD estimation. The support used for the immobilization in the present invention confers high stability, viability and negligible leaching to the biocatalyst i.e., microorganisms. This can be attributed to the fact that the biocatalysts immobilized in hydrophilic supports under hydrophobic conditions confer least leaching to the immobiliezed biocatalyst.

There is no prior art for the development of cell beads sensor using agarose as a support, for instant BOD estimation. On the contrary, there is only one report for the development of cell beads sensor for instant BOD estimation using supports other than agarose, such as κ-carrageenan under hydrophilic conditions. The limitations of such developed sensor is that it is used only for the BOD estimation of glucose-glutamic acid (GGA) covening a very low range i.e., up to a concentration of 24 mg/l. The cell beads BOD sensor developed in the present invention can instantly estimate BOD of higher GGA concentrations (i.e., up to 300 mg/l), covering a wide range of synthetic samples (peptone, glucose, glutamic acid and citric acid) as well as a range of highly, moderately and low biodegradable industrial effluents.

The reproducibility of cell beads sensor can only be obtained if a defined microbial consortium is used as a biocatalyst, because sensors based on single organisms or microbial consortium isolated from activated sludge exhibit erroneous results. Further, they do not respond to higher GGA concentrations and a range of synthetic and industrial samples. Such specific microbial consortium based cell beads sensors may also find great applications in on-line monitoring of the degree of pollutional strength in a wide variety of industrial waste-waters within a very short time, which is very essential for combating the problem of water pollution. The said microbial consortium is capable of assimilating most of the organic matter present in different industrial effluents.

OBJECTS OF THE INVENTION

The main object of the present invention is to provide cell beads BOD sensor useful for instant BOD estimation.

Another object of the present invention is to provide a microbial consortium exerting a synergistic effect, capable of assimilating a variety of synthetic samples and industrial effluents.

Still another object of the present invention, is to provide a support for immobilization, which is non-toxic to the formulated microbial consortium and causes least physical and chemical damages to the microbial cells.

Yet another object of the present invention, is to provide a process for the preparation of cell beads useful for instant monitoring of BOD load of a wide range of synthetic samples as well as industrial effluents with low, moderate and high BOD load.

SUMMARY OF THE INVENTION

The present invention provides cell beads incorporating a formulated microbial consortium and a process for the preparation of the said cell beads useful for instant BOD estimation of a wide range of synthetic samples and industrial effluents with low, moderate and high BOD load.

DETAILED DESCRIPTION OF THE INVENTION

Accordingly the present invention provides bacteria namely *Aeromonas sobria, Enterobacter sakazaki, Pseudomonas aeruginosa* useful in the estimation of BOD, which have been deposited in the Center for Biochemical Technology, New Delhi, India, and either Deutsche Sammlung Von Mikroorganismen Und Zelikulturen GmbH Braunschweig, Germany, or the American Type Culture Collection, Manassas, Va. and given accession nos. CBTCC/Micro/13 (DSM 15063) having characteristics similar to that of prior art strain (ATCC 35993), CBTCC/Micro/6 (DSM 15078) having characteristics similar to that of prior art strain (ATCC 12868) and CBTCC/Micro/3 (PTA-3748) having characteristics similar to that of prior art strain (ATCC 49622) respectively. The deposits with the Deutsche Sammlung Von Mikroorganismen Und Zellkulturen GmbH and the American Type Culture Collection were made in compliance with the Budapest Treaty on the International Recognition of the Deposit of Microorganisms for the Purposes of Patent Procedure on the following dates:

| Initial Accession No. | Budapest Accession No. | Date of Deposit |
| --- | --- | --- |
| CBTCC/MICRO/13 | DSM 15063 | May 28, 2002 |
| BTCC/MICRO6 | DSM 15078 | May 28, 2002 |
| CBTCC/MICRO/3 | PTA-3748 | Aug. 27, 2001 |

The deposits with the American Type Culture Collection, Manassas, Va. identified by ATCC Nos. 35993, 12868, and 49622 are publicly available as non-patent deposits.

The microbial consortium provided according to the present invention contains bacteria consisting of:

Prior art strains having characteristics similar to that of CBTCC No.

| Sl. No. | Cultures | Accession No. | |
| --- | --- | --- | --- |
| 1. | Aeromonas sobria | CBTCC/MICRO/13 (DSM 15063) | ATCC 35993 |
| 2. | Enterobacter sakazaki | CBTCC/MICRO/6 (DSM 15078) | ATCC 12868 |
| 3. | Pseudomonas aeruginosa | CBTCC/MICRO/3 (PTA-3748) | ATCC 49622 |

Wherein, said strains are selected from the given isolated bacteria, viz.,

Prior art strains having characteristics similar to that of CBTCC No.

| Sl. No. | Cultures | Accession No. | |
| --- | --- | --- | --- |
| 1. | Yersinia enterocolitica | CBTCC/MICRO/4 | ATCC 27739 |
| 2. | Aeromonas sobria | CBTCC/MICRO/13 (DSM 15063) | ATCC 35993 |
| 3. | Klebsiella pneumoniae | CBTCC/MICRO/14 | ATCC 13906 |
| 4. | Serratia liquefaciens | CBTCC/MICRO/7 | ATCC 25641 |
| 5. | Enterobacter sakazaki | CBTCC/MICRO/6 (DSM 15078) | ATCC 12868 |
| 6. | Citrobacter amalonaticus | CBTCC/MICRO/2 | ATCC 25406 |
| 7. | Pseudomonas flourescens | CBTCC/MICRO/11 | ATCC 13525 |
| 8. | Pseudomonas aeruginosa | CBTCC/MICRO/3 (PTA-3748) | ATCC 49622 |
| 9. | Enterobacter cloacae | CBTCC/MICRO/1 | ATCC 29893 |
| 10. | Acinetobacter calcoaceticus | CBTCC/MICRO/15 | ATCC 31012 | which, facilitate the process of testing, giving instant BOD results of a wide variety of industrial effluents, performed at any place. Above microorganisms are deposited at Center for Biochemical Technology Culture Collection (CBTCC) designated as stated above and will be made available to public on request as per the normal official procedures.

The main characteristic features of all the bacterial cultures used for the invention, which are similar to that of ATCC cultures are given below:

Characteristic features of *Aeromonas sobria* (CBTCC/MICRO/13, DSM 15063)

Facultative anaerobic gram negative rods,

Motile with a single polar flagellum,

Oxidase and catalase positive,

Omithine decarboxylase, urease and phenylalanine deaminase negative, and

Arginine dihydrolase, gelatinase and DNase positive.

Characteristic features of *Enterobacter sakazaki*(CBTCC/MICRO/6, DSM 15078)

Gram-negative, facultative anaerobic rods,

Motile with peritrichous flagella and chemoorganotrophic,

Indole negative, Voges-Proskauer and citrate positive,

Arginine dihydrolase and omithine decarboxylase positive,

Oxidase and urease negative, and

Produces yellow pigment at 25° C.

Characteristic features of *Pseudomonas aeruginosa* (CBTCC/MICRO/3, PTA-3748)

Gram negative, aerobic rod shaped bacteria,

Have polar flagella,

Metabolism is respiratory, never fermentative,

Oxidase positive,

Catalase positive, and

Denitrification positive.

The immobilized cell beads may contain the bacteria, in a preferred embodiment of the invention, in uniform amounts.

The cell beads of the present invention arc useful for instant BOD estimation.

The bacterial cultures of the above immobilized cell beads are isolated from sewage. Sewage samples are collected from Dhirpur Sewage Treatment Plant, Delhi, India. Sewage is homogenized for 2 minutes and suspended in nutrient broth. Incubation is carried out for 24 hours. Cultures are plated on nutrient agar. Colonies are mixed on a vortex mixer and all the cultures are isolated in pure form after several sub-cultures.

In the present invention, the cell beads are prepared by inoculating individual bacterial strains of the above mentioned bacteria separately in nutrient broth containing (per liter), 5.0 g peptic digest of animal tissue, 5.0 g of sodium chloride, 1.5 g of beef extract, 1.5 g yeast extract and 0.1 ml tween-80. Incubation of all the cultures is done preferably at a temperature of 37° C. for approximately 12–24 hours, under gentle shaking. Optical density of all the cultures is measured at 620 nm after stipulated time intervals. After attaining sufficient growth on the basis of optical density, the individual cultures are mixed in equal proportions for formulating desired microbial consortium. The resultant cell suspension is centrifuged at an appropriate rpm for a period of 20 minutes at a temperature ranging between 1–10° C. The resultant pellet is washed by dissolving in minimum quantity of phosphate buffer, 50 mM, pH 6.8 and recentrifuged at an appropriate rpm, preferably at 8000 rpm for a period of approximately 20 minutes at a temperature ranging between 1–10° C. Immobilization of the obtained pellet is done using various supports such as agarose, sodium alginate, sodium alginate+polyvinyl alcohol (PVA).

The formulated microbial consortium was immobilized in agarose by dissolving the pellet of individual microorganisms as well as of the formulated microbial consortium is dissolved in 1.0 ml of phosphate buffer, 50 mM, pH6.8 and then mixed with 3% agarose. The resultant cell slurry is extruded drop wise with the help of a 10 ml syringe in 250 ml of mustard oil kept at 4° C. The cell slurry is extruded as discrete droplets so as to form beads of appropriate size. The beads thus formed are washed with petroleum ether to remove the adhering oil and then washed with 50 mM phosphate buffer, pH 6.8 three to five times. The immobilized microbial beads thus obtained are stored at a temperature preferably 4° C. in 50 mM phosphate buffer, pH 6.8 till further use.

The immobilization of microbial consortium in sodium alginate is affected by mixing the cell pellet in 2% sodium alginate solution and extruding the resultant slurry into a stirred 12 mM $CaCl_2$ solution. The beads thus formed are left in 12 mM $CaCl_2$ solution for approximately 3 hours and later washed with 50 mM phosphate buffer, pH 6.8. The immobilized microbial beads are stored in 50 Mm $CaCl_2$ solution at a temperature preferably at 4° C.

For the preparation of beads in alginate+polyvinyl alcohol, 15% of polyvinyl alcohol and 2% sodium alginate were dissolved in sterilized 50 mM phosphate buffer, pH6.8. The cell pellet is mixed with the above said solution and the resultant cell slurry is extruded drop wise with the help of a 10 ml syringe in saturated boric acid solution. The beads are removed and kept in 1.0M $NaH_2PO_4$ for 30–45 minutes for hardening. The immobilized microbial beads thus obtained are stored in 50 mM phosphate buffer, pH6.8 at a temperature preferably 4° C.

The viability, stability and leaching of the immobilized microbial beads is checked at regular time intervals. For checking the viability of the immobilized microbial beads, the beads are added in nutrient broth and incubated at 37° C., 120 rpm for 6–8 hours. A loopful of the incubated broth is streaked on nutrient agar plates and incubated at 37° C. overnight. The colonies are observed for growth on agar plates. For the stability studies the formulated microbial beads are stored at 4° C. in 50 mM phosphate buffer, pH6.8. Stability is observed in terms of response at regular time intervals. Leaching of the prepared beads is checked by measuring the optical density of the storage buffer at stipulated time intervals.

For instant BOD estimation, known amount of the prepared cell beads is added into a continuously stirred 50 mM phosphate buffer solution, pH6.8 with a dissolved oxygen probe immersed in the system. The experiment is set-up in a system, which is not of flow through type.

The response was measured in terms of change in current, which was observed using an amperometric system consisting of a dissolved oxygen probe attached to a multimeter. For measuring the current an external polarization voltage of −0.65 volts was applied to the cathode.

The immobilized cell beads were checked for their response in terms of change in current using GGA as a reference standard in BOD analysis. For this, the electrode is dipped in stirred phosphate buffer solution, 50 mM, pH6.8 containing the immobilized microbial beads. After a stable current is obtained, known strength of GGA is injected into the reaction assembly. Consumption of oxygen by the microbial cells immobilized in beads causes a decrease in dissolved oxygen in the system. This is elucidated by a gradual decrease in current until a stable value is attained. The steady state indicates that the consumption of oxygen by the immobilized cell beads and the diffusion of oxygen from the solution to the beads is in equilibrium. As observed in the present course of study, the change in current is linearly related to GGA standard over the range of 30–300 mg/l.

Accordingly, the invention provides immobilized cell beads comprising a synergistic mixture of the following isolated bacterial strains present in equal proportions useful for instant BOD estimation.

Prior art strains having characteristics similar to that of CBTCC No.

| Sl. No. | Cultures | Accession No. | |
|---|---|---|---|
| 1. | Aeromonas sobria | CBTCC/MICRO/13 (DSM 15063) | ATCC 35993 |
| 2. | Enterobacter sakazaki | CBTCC/MICRO/6 (DSM 15078) | ATCC 12868 |
| 3. | Pseudomonas aeruginosa | CBTCC/MICRO/3 (PTA-3748) | ATCC 49622 |

Prior art strains having characteristics similar to that of CBTCC No.

| Sl. No. | Cultures | Accession No. | |
|---|---|---|---|
| 1. | Yersinia enterocolitica | CBTCC/MICRO/4 | ATCC 27739 |
| 2. | Aeromonas sobria | CBTCC/MICRO/13 (DSM 15063) | ATCC 35993 |
| 3. | Klebsiella pneumoniae | CBTCC/MICRO/14 | ATCC 13906 |
| 4. | Serratia liquefaciens | CBTCC/MICRO/7 | ATCC 25641 |
| 5. | Enterobacter sakazaki | CBTCC/MICRO/6 (DSM 15078) | ATCC 12868 |
| 6. | Citrobacter amalonaticus | CBTCC/MICRO/2 | ATCC 25406 |
| 7. | Pseudomonas fluorescens | CBTCC/MICRO/11 | ATCC 13525 |
| 8. | Pseudomonas aeruginosa | CBTCC/MICRO/3 (PTA-3748) | ATCC 49622 |
| 9. | Enterobacter cloaca | CBTCC/MICRO/1 | ATCC 29893 |
| 10. | Acinetobacter calcoaceticus | CBTCC/MICRO/15 | ATCC 31012 |

The cell beads as obtained are stable at a temperature ranging from 4 to 15° C.

The invention further provides a process for the preparation of immobilized cell beads useful for instant BOD estimation of a wide range of synthetic samples and industrial effluents, using a dissolved oxygen probe, which comprises:

1. inoculating the selected individual microorganisms of the microbial consortium in nutrient medium and incubating them at an ambient temperature under gentle agitation for a period of 12 hours;
2. mixing the cell suspensions of individual microorganisms in equal proportions based on optical density values at 620 nm;
3. harvesting the cells of the microbial consortium obtained in step(b) by centrifuging for 20–30 minutes at a temperature preferably at 4° C.;
4. washing the pellet obtained from step(c) by dissolving in 10–100 mM phosphate buffer, pH 6.5–7.5 and recentrifuging the pellet;
5. dissolving the pellet obtained from step (d) in 2.5 ml of 10–100 mM phosphate buffer, pH 6.5–7.5 to obtain cell slurry for immobilization;
6. mixing the cell slurry obtained from step (e) with an appropriate immobilizing agent i.e., agarose and extruding the said slurry drop wise in mustard oil kept at a temperature preferably at 4° C. to get cell beads;
7. washing the beads obtained from step (f) with petroleum ether and rewashing the washed beads with 10–100 mM phosphate buffer, pH 6.5–7.5;
8. storing the washed beads obtained from step (g) in 10–100 mM phosphate buffer, pH 6.5–7.5 at a temperature preferably at 4° C.;
9. checking the growth potential i.e., viability of the said cell beads obtained from step (h);
10. adding 20.0 g beads in 100 ml of 10–100 mM phosphate buffer, pH 6.5–7.5 and immersing a dissolved oxygen probe to obtain a closed system;
11. applying an external polarization voltage of −0.65 volts to the said system obtained from step (j);
12. attaining a stable current in the said system obtained from step (k) and adding different concentrations of GGA ranging from 30–300 mg/l into the said system for instant BOD estimation;
13. checking the stability of the selected cell beads obtained from step (i) using the system obtained from step (l);
14. testing the cell beads obtained from step (m) for instant BOD estimation with different synthetic samples viz., glucose, glutamic acid, peptone and citric acid;
15. testing the said cell beads for instant BOD estimation of industrial effluents having low, moderate and high biodegradable organic matter.

In an embodiment of the present invention, a microbial consortium comprising a synergistic mixture of the bacterial strains, viz., *Enterobacter sakazaki, Pseudomonas aeruginosa* and *Aeromonas sobria* is formulated.

In another embodiment of the present invention, the individual bacterial strains of the above mentioned formulated microbial consortium are inoculated separately and incubated at 30–37° C. for 16–24 hours at 100–150 rpm.

In yet another embodiment of the present invention, the cell suspensions of the individual bacterial strains are mixed in equal proportions based on their optical density values at 600–650 nm.

In a further embodiment of the present invention, the mixed cell suspension is centrifuged at an appropriate rpm, preferably at 8,000–12,000 rpm for a period of approximately 20–30 minutes at a temperature ranging between 4–8° C.

In another embodiment of the present invention, the resultant pellet is washed by dissolving in appropriate quantity of phosphate buffer, 10–100 mM, pH 6.5–7.5 and recentrifuged at an appropriate rpm in the range of 8,000–12,000 rpm for 20–30 minutes at a temperature preferably at 4° C.

In yet another embodiment of the present invention, the obtained pellet is mixed with 1–4% of an appropriate immobilizing agent i.e., agarose.

In one of the embodiments of the present invention, the immobilization of the resulting cell slurry is carried out by extruding the slurry drop wise in mustard oil, kept at a temperature, preferably at 1–10° C.

In one of the embodiment of the invention, the ratio of agrose to mustard oil is in the range between 1:2.5 to 1:5.

In still another embodiment of the present invention, the obtained cell beads are first washed with petroleum ether and then re-washed 3–5 times with 10–100 mM, phosphate buffer, pH 6.5–7.5.

In another embodiment of the present invention, the washed immobilized cell beads are stored in phosphate buffer, 10–100 mM, pH 6.5–7.5, at a temperature ranging between 1–4° C.

In a further embodiment of the present invention, the prepared cell beads are incubated in 50–100 ml of nutrient broth, a loopful of which is streaked on nutrient agar plates. The streaked plates are incubated at 37° C. for 16–20 hours to observe colony formation for checking the viability of the prepared cell beads.

The invention further provides a method for instant BOD estimation which comprises immobilized cell beads.

In still another embodiment of the present invention, 5.0–25.0 g of cell beads are added in 50–100 ml of 10–100 mM phosphate buffer, pH 6.5–7.5 and for measuring the response, a dissolved oxygen probe is immersed in the system.

In yet another embodiment of the present invention, an external voltage of −0.6 to −0.65 volts is applied to the system for the reduction of oxygen at cathode.

In another embodiment of the present invention, a stable current is attained in the said system and GGA concentrations ranging between 30–300 mg/l are added, for instant BOD estimation using the said cell beads.

In one of the embodiments of the present invention, the prepared cell beads were tested for instant BOD estimation using a range of synthetic samples, i.e., Glucose, Glutamic acid, Peptone and Citric acid.

In still another embodiment of the present invention, the said cell beads were used for instant BOD estimation of a range of industrial effluents covering low, moderate and highly biodegradable samples.

Yet, another embodiment provides a process, wherein a dissolved oxygen probe is used as a sensor to sense the dissolved oxygen content in the system in terms of current (nA).

The invention further described with references to the examples given below and shall not be construed to limit the scope of invention.

Selection of Hydrophobic Solvent for Immobilization

Example I (Comparative Example)

A number of bacteria namely, *Yersinia enterocolitica, Aeromonas sobria, Klebsiella pneumoniae, Serratia liquefaciens, Enterobacter sakazaki, Citrobacter amalonaticus, Pseudomonas fluorescens, Pseudomnonas aeruginosa, Enterobacter cloacae, Acinetobacter calcoaceticus* were used for the preparation of cell beads. For this, individual bacterial strains were inoculated in 50 ml nutrient broth with 0.01% tween-80. All the cultures were incubated at 37° C. for 16–20 hours in an incubator shaker at 120 rpm. Optical density of all the cultures was maintained to 1.0.

Cells were harvested by centrifuging the bacterial suspension at 10,000 rpm for 20 minutes at 4° C. The pellet obtained was suspended in 1.0–2.0 ml of 10–100 mM phosphate buffer, pH 6.8 and recentrifuged at 10,000 rpm for 20 minutes at 4° C. The resultant pellet of individual bacteria was mixed with 3% agarose and extruded drop wise in castor oil kept at a temperature ranging between 4° C.–8° C. The cell beads were first washed with petroleum ether and then rewashed 3–5 times with 10–100 mM phosphate buffer, pH 6.5–7.5. The cell beads thus obtained were stored in 10–100 mM phosphate buffer, pH 6.5–7.5 at a temperature preferably at 4° C. The beads obtained were irregular in shape and had a tail.

Example II (Comparative Example)

A number of bacteria namely, *Yersinia enterocolitica, Aeromonas sobria, Klebsiella pneumoniae, Serratia liquefaciens, Enterobacter sakazaki, Citrobacter amalonaticus, Pseudomonas fluorescens, Pseudomonas aeruginosa, Enterobacter cloaca, Acinetobacter calcoaceticus* were used for the preparation of cell beads. For this, individual bacterial strains were inoculated in 50 ml nutrient broth with 0.01% tween-80. All the cultures were incubated at 37° C. for 16–24 hours in an incubator shaker at 150 rpm. Optical density of all the cultures was maintained to 1.0. Cells were harvested by centrifuging the bacterial suspension at 7500 rpm for 30 minutes at 4° C. The pellet obtained was suspended in 1.0–2.0 ml of 10–100 mM phosphate buffer, pH 6.8 and recentrifuged at 7500 rpm for 30 minutes at 4° C. The resultant pellet of individual bacteria was mixed with 3% agarose and extruded drop wise in vegetable oil kept at a temperature ranging between 4° C.–8° C. The cell beads were first washed with petroleum ether and then rewashed 3–5 times with 10–100 mM phosphate buffer, pH 6.5–7.5. The cell beads thus obtained were stored in 10–100 mM phosphate buffer, pH 6.5–7.5 at a temperature preferably at 4° C. The beads obtained were very fragile and were not spherical. In addition to beads, lump formation was also observed.

Example III (Comparative Example)

A number of bacteria namely, *Yersinia enterocolitica, Aeromonas sobria, Klebsiella pneumoniae, Serratia liquefaciens, Enterobacter sakazaki, Citrobacter amalonaticus, Pseudomonas fluorescens, Pseudomonas aeruginosa, Enterobacter cloaca, Acinetobacter calcoaceticus* were used for the preparation of cell beads. For this, individual bacterial strains were inoculated in 50 ml nutrient broth with 0.01% tween-80. All the cultures were incubated at 37° C. for 16–18 hours in an incubator shaker at 150 rpm. Optical density of all the cultures was maintained to 1.0. Cells were harvested by centrifuging the bacterial suspension at 8000 rpm for 20 minutes at 4° C. The pellet obtained was suspended in 1.0–2.0 ml of 10–100 mM phosphate buffer, pH 6.8 and recentrifuged at 8000 rpm for 20 minutes at 4° C. The resultant pellet of individual bacteria was mixed with 3% agarose and extruded drop wise in mustard oil kept at a temperature ranging between 4° C.–8° C. The cell beads were first washed with petroleum ether and then rewashed 3–5 times with 10–100 mM phosphate buffer, pH 6.5–7.5. The cell beads thus obtained were stored in 10–100 mM phosphate buffer, pH 6.5–7.5 at a temperature preferably at 4° C. The beads obtained were spherical, porous and stable and were used for further study.

Preparation of Closed System for Instant BOD Estimation

EXAMPLE IV

Appropriate amount of the prepared cell beads was added in stirred phosphate buffer solution. For measuring the response a commercially available 'DO' probe was immersed in the system. The system was covered with parafilm to render it a closed system. The probe was attached with a multimeter to note the readings. An external polarization voltage of −0.65 volts was applied to the system to provide the reduction of oxygen at the cathode.

Selection of Microorganisms for the Formulation of Different Microbial Consortium

EXAMPLE V

The individual microorganisms incorporated in porous, stable and spherical cell beads obtained using 3% agarose in mustard oil were selected for instant BOD estimation in closed system, using a range of GGA concentrations (30–300 mg/l) as shown in Table 1.

TABLE 1

BOD values of a range of GGA concentrations using cell beads of individual bacteria

| Cell beads of bacteria | BOD values (mg/l) of GGA conc. (mg/l) | | | | | | |
|---|---|---|---|---|---|---|---|
| | 30 | 60 | 90 | 120 | 180 | 240 | 300 |
| *Yersinia enterocolitica* | 19 | 39 | 60 | 82 | 126 | 154 | 196 |
| *Aeromonas sobria* | 24 | 46 | 70 | 92 | 139 | 183 | 218 |
| *Klebsiella pneumoniae* | 16 | 38 | 62 | 79 | 123 | 165 | 201 |
| *Serratia liquefaciens* | 11 | 28 | 51 | 74 | 119 | 156 | 183 |
| *Enterobacter sakazaki* | 21 | 45 | 63 | 59 | 142 | 179 | 228 |
| *Citrobacter amalonaticus* | 07 | 22 | 47 | 69 | 108 | 149 | 174 |
| *Pseudomonas fluorescens* | 18 | 40 | 59 | 78 | 124 | 163 | 204 |
| *Pseudomonas aeruginosa* | 19 | 39 | 67 | 85 | 127 | 167 | 212 |
| *Enterobacter cloaca* | 17 | 39 | 60 | 82 | 131 | 175 | 205 |
| *Acinetobacter calcoaceticus* | 13 | 28 | 42 | 71 | 128 | 155 | 198 |

Table 1 represents the BOD values of GGA ranging from 30–300 mg/l observed from cell beads prepared using individual bacteria. Out of all the bacterial strains evaluated for BOD estimation, bacterial strains, namely, *Aeromonas sobria, Klebsiella pneumoniae, Enterobacter sakazaki, Pseudomonas fluorescens, Pseudomonas aeruginosa* and *Enterobacter cloaca* showed BOD values equivalent to BOD values obtained using sewage.

EXAMPLE VI

Out of the total individual bacterial cell beads used for instant BOD estimation, bacteria namely *Aeromonas sobria, Klebsiella pneumoniae, Enterobacter sakazaki, Pseudomonas fluorescens, Pseudomonas aeruginosa* and *Enterobacter cloaca* were selected for the formulation of different microbial consortia based on the BOD results.

Selection of Microbial Consortium for the Preparation of Cell Beads for Instant BOD Analysis Random combination of microorganisms were chosen for the formulation of different microbial consortia (I–VI).

Example VII (Comparative Example)

Microbial consortium I comprised of six bacterial strains namely, *Aeromonas sobria, Klebsiella pneumoniae, Enterobacter sakazaki, Pseudomonas fluorescens, Pseudomonas aeruginosa* and *Enterobacter cloaca* and was used for the preparation of cell beads. Instant BOD analysis of a range of GGA concentrations ranging from 30–300 mg/l was carried out using the said cell beads. Table2 depicts the BOD values of GGA concentrations using the cell beads comprising the microbial consortium I.

Example VIII (Comparative Example)

Microbial consortium II comprised of five bacterial strains namely, *Aeromonas sobria, Enterobacter sakazaki, Pseudomnonas fluorescens, Pseudomonas aeruginosa* and *Enterobacter cloaca* and was used for the preparation of cell beads. The prepared cell beads were used for the instant BOD analysis of GGA concentrations ranging from 30–300 mg/l. Table2 depicts the BOD values of GGA concentrations using the cell beads comprising the microbial consortium I.

Example IX (Comparative Example)

Microbial consortium III comprised of four bacterial strains namely, *Aeromonas sobria, Enterobacter sakazaki, Pseudomonas aeruginosa* and *Enterobacter cloaca* and was used for the preparation of cell beads. The prepared cell beads were used for instant BOD estimation of GGA concentrations covering a range of 30–300 mg/l. Table2 shows BOD values of GGA upto a concentration of 300 mg/l using the prepared cell beads.

Example X (Comparative Example)

Microbial consortium IV comprised of three bacterial strains namely, *Pseudomonas fluorescens, Klebsiella pneumoniae* and *Enterobacter cloaca* and was used for the preparation of cell beads. The prepared cell beads were used for the instant BOD analysis of GGA concentrations ranging from 30–300 mg/l. Table2 depicts the BOD values of GGA concentrations using the cell beads comprising the microbial consortium IV.

Example XI (Comparative Example)

Microbial consortium V comprised of three bacterial strains namely, *Enterobacter sakazaki, Aeromonas sobria* and *Pseudomonas aeruginosa* and was used for the preparation of cell beads. Instant BOD analysis of a range of GGA concentrations ranging from 30–300 mg/l was carried out using the said cell beads. Table2 depicts the BOD values of GGA concentrations using the cell beads comprising the microbial consortium V.

Example XII (Comparative Example)

Microbial consortium VI comprised of three bacterial strains namely, *Enterobacter sakazaki, Klebsiella pneumoniae* and *Enterobacter cloaca* and was used for the preparation of cell beads. The prepared cell beads were used for instant BOD estimation of GGA concentrations covering a range of 30–300 mg/l. Table2 shows BOD values of GGA upto a concentration of 300 mg/l using the prepared cell beads.

TABLE 2

BOD values (mg/l) of CGA with the prepared cell beads of microbial consortia I, II, III, IV, V and VI Observed BOD values

| | | By Cell beads sensor (mg/l) | | | | | |
|---|---|---|---|---|---|---|---|
| GGA conc. (mg/l) | By Standard Conventional method (mg/l) | Microbial Consortium I | Microbial Consortium II | Microbial Consortium III | Microbial Consortium IV | Microbial Consortium V | Microbial Consortium VI |
| 30 | 17 | 10 | 09 | 11 | 16 | 21 | 13 |
| 60 | 56 | 21 | 18 | 19 | 35 | 42 | 30 |
| 90 | 68 | 48 | 54 | 50 | 54 | 67 | 49 |
| 120 | 90 | 67 | 75 | 69 | 69 | 83 | 60 |
| 180 | 135 | 118 | 121 | 123 | 103 | 129 | 97 |
| 240 | 176 | 137 | 143 | 148 | 140 | 162 | 121 |
| 300 | 214 | 163 | 169 | 161 | 168 | 198 | 147 |

EXAMPLE XIII

Out of the six microbial consortia formulated for the preparation of cell beads, microbial consortium V comprising of the bacterial strains, namely, *Enterobacter sakazaki, Pseudomonas aeruginosa* and *Aeromonas sobria* was selected on the basis of the BOD values of GGA (30–300 mg/l) for further study.

Storage Conditions of the Selected Cell Beads

EXAMPLE XIV

The selected immobilized microbial consortium was stored at different temperatures i.e., 4° C. to 37° C. for stability and viability studies.

It was observed that the cell beads stored at 4° C. were more stable than the cell beads stored at other temperatures. In addition, the cell beads stored at 4° C. were more viable in comparison to beads stored at temperature higher than 4° C.

Instant BOD Analysis of Synthetic Samples Using the Selected Cell Beads Sensor

EXAMPLE XV

Cell beads selected for the present invention were used for the instant BOD estimation of different synthetic samples, e.g., glucose, glutamic acid, peptone and citric acid as described in example IV. 3000 mg/l each of the respective synthetic samples were used for instant BOD estimation.

Table 3 represents the BOD values of the above mentioned synthetic samples using the cell beads sensor. All the experiments of the present invention were carried out three times to obtain reproducibility and the mean values of all the experiments were taken into consideration. The results obtained were compared with BOD values obtained using the conventional method.

TABLE 3

BOD values of the synthetic samples (300 mg/l) observed with the prepared cell beads BOD sensor

| Sample | BOD values as observed by conventional method (mg/l) | BOD values as observed by cell beads sensor (mg/l) |
| --- | --- | --- |
| Glucose | 189 | 193 |
| Glutamic acid | 165 | 168 |
| Peptone | 195 | 204 |
| Citric acid | 166 | 143 |

Instant BOD Analysis of Industrial Samples Using the Selected Cell Beads Sensor

EXAMPLE XVI

The selected cell beads of the present invention were also used for the instant BOD estimation of a wide range of industrial samples covering low, moderate and highly biodegradable organic matter as described in example IV. The samples were collected afresh for instant BOD estimation. Table 4 represents that BOD values of all the industrial waste-waters used for the study by selected cell beads BOD sensor.

TABLE 4

Instant BOD estimation of industrial effluents with the cell beads sensor

| Industrial waste-water | Observed BOD values (mg/l) | |
| --- | --- | --- |
| | By conventional method | By cell beads sensor |
| Low BOD load | 364 | 328 |
| Moderate BOD load | 996 | 1,025 |
| High BOD load | 54,200 | 53,110 |

Advantages

1. The prepared immobilized cell beads when used in conjunction with an electronic device are capable of determining the BOD load of waste-waters instantly i.e., within 30–45 minutes as compared to the conventional method which gives BOD values within 3–5 days.
2. The formulated selected microbial consortium of cell beads acts in a synergistic way and is capable of assimilating a vast array of organic compounds present in different types of industrial effluents.
3. The method of gelling agarose in cold mustard oil, described in the invention, is novel and cost effective.
4. The method adopted for immobilizing the microorganisms is entrapment, which causes least physical and chemical damage to the immobilized entity.
5. The support used for immobilization i.e. agarose is non-toxic to micro-organisms. Moreover, agarose is not utilizable by the microbial consortium in use, thereby not adding to BOD of the sample in any way.
6. The prepared immobilized cell beads have long stability, viability and negligible leaching as compared to cell beads prepared using other supports.
7. The immobilized microbial beads described in the invention do not act as barrier for the diffusion of oxygen through them, thereby aiding in instant BOD estimation.

What is claimed is:

1. A process for the preparation of immobilized cell beads which comprises:

a) inoculating selected individual microorganisms of a microbial consortium in nutrient medium and incubating them at an ambient temperature under gentle agitation for a period of up to 12 hours to obtain cell suspensions;

b) mixing the cell suspensions of individual microorganisms in equal proportions based on optical density values at 600–650 nm;

c) harvesting cells of the microbial consortium obtained in step (b) by centrifuging for 20–30 minutes at a temperature of 40° C. to make a pellet;

d) washing the pellet obtained from step (c) by suspending the pellet in 10–100 mM phosphate buffer, pH 6.5–7.5 and recentrifuging the pellet;

e) resuspending the pellet obtained from step (d) in 10–100 mM phosphate buffer, pH 6.5–7.5 to obtain a cell slurry for immobilization;

f) mixing the cell slurry obtained from step (e) with an appropriate amount of immobilizing agent and extruding the said slurry dropwise in 250–300 ml of mustard oil kept at a temperature between 1–100° C. to obtain beads;

g) washing the beads obtained from step (f) with petroleum ether and rewashing the washed beads with 10–100 mM phosphate buffer, pH 6.5–7.5;

h) storing the washed beads obtained from step (g) in 10–100 mM phosphate buffer, pH 6.5–7.5 at a temperature of 4° C.;

i) checking the growth potential, i.e. viability, of said cell beads obtained from step (h);

j) adding the prepared cell beads in 10–100 mM of stirred phosphate buffer solution, pH 6.5–7.5 and immersing a dissolved oxygen probe in a non-flow through type of system;

k) applying an external polarization voltage of −0.6 to −0.65 volts to said system obtained from step (j);

l) attaining a stable current in said system obtained from step (k) and adding different concentrations of glucose-glutamic acid (GGA) ranging from 30–300 mg/l into the said system for instant BOD estimation;

m) checking the stability of the selected cell beads obtained from step (i) using the system obtained from step (l);

n) testing the cell beads obtained from step (m) for instant BOD estimation with different synthetic examples viz., glucose, glutamic acid, peptone and citric acid; and o) testing said cell beads for instant BOD estimation of industrial effluents having low, moderate and high biodegradable organic matter;

wherein the microbial consortium comprises (1) a strain of *Aeromonas sobria* having the following characteristics;

i) facultatively anaerobic gram negative rods;
ii) motile with a single polar flagellum;
iii) oxidase and catalase positive;
iv) ornithine decarboxylase, urease, and phenylalanine deaminase negative; and
v) arginine dihydrolase, gelatinatse and DNase positive;

(2) a strain of *Enterobacter sakazaki* having the following characteristics;

i) gram-negative facultatively anaerobic rods;
ii) motile with peritrichous flagella and chemoorganotrophic;
iii) indole negative, Voges-Proskaur and citrate positive;

iv) arginine dihydrolase and ornithine decarboxylase positive;
v) oxidase and urease negative; and
vi) produces yellow pigment at 25° C.; and
(3) a strain of *Pseudomonas aeruginosa* having the following characteristics;
i) gram-negative, aerobic rod shaped bacteria;
ii) have polar flagella;
iii) metabolism is respiratory, never fermentative;
iv) oxidase positive;
v) catalase positive; and
vi) dentrification positive.

2. A process as claimed in claim 1, wherein the individual bacterial strains, namely *Aeromonas sobria, Enterobacter sakazaki,* and *Pseudomonas aeruginosa* selected for the formulation of microbial consortium and inoculated separately in nutrient broth medium are as follows:

| Culture | Alternative Accession Nos. |
| --- | --- |
| *Aeromonas sobria* | CBTCC/MICRO/13, DSM 15063, or ATCC 35993 |
| *Enterobacter sakazaki* | CBTCC/MICRO/6, DSM 15078, or ATCC 12868 |
| *Pseudomonas aeruginosa* | CBTCC/MICRO/3, PTA-3748, or ATCC 49622 |

3. A process as claimed in claim 1, wherein the incubation of the individually inoculated bacterial strains is carried out at a temperature ranging from 30–37° C. at 75–175 rpm for a period of 8–20 hours.

4. A process as claimed in claim 1, wherein the cell suspension of individual bacteria are mixed in equal proportions on the basis of their optical density values at 600–650 nm.

5. A process as claimed in claim 1, wherein the microbial consortium is centrifuged at 8000–12,000 rpm for 20–30 minutes at a temperature ranging between 4–8° C.

6. A process as claimed in claim 1, wherein in step (d) the cell pellet is suspended in 10–50 ml of 10–100 mM phosphate buffer, pH 6.5–7.5 for washing.

7. A process as claimed in claim 1, wherein the dissolved cell pellet is centrifuged at 8000–12,000 rpm for 20–30 minutes at a temperature ranging between 4–8° C.

8. A process as claimed in claim 1, wherein in step (e) the washed cell pellet is resuspended in 1.0–5.0 ml of 10–100 mM phosphate buffer, pH 6.5–7.5 to obtain a cell slurry for immobilization.

9. A process as claimed in claim 1, wherein the cell slurry is mixed with 1–4% of an appropriate immobilizing agent i.e., agarose, and extruded drop wise in mustard oil kept at a temperature ranging between 1–10° C.

10. A process as claimed in claim 1, wherein the ratio of agrose to mustard oil is in the range between 1:2.5 to 1:5.

11. A process as claimed in claim 1, wherein the immobilized cell beads are washed with 100–250 ml of petroleum ether and re washed with 10–100 mM phosphate buffer, pH 6.5–7.5.

12. A process as claimed in claim 1, wherein the washed cell beads are stored in 10–100 mM phosphate buffer, pH 6.5–7.5 at a temperature ranging between 4–10° C.

13. A process as claimed in claim 1, wherein the viability of the prepared cell beads is checked by incubating in 5.0–25.0 ml of nutrient broth medium at a temperature ranging between 30–37° C. for a period of 6–8 hours.

14. A process as claimed in claim 1, wherein 5.0–25.0 g of the cell beads are added in 20–100 ml of 10–100 mM phosphate buffer, pH 6.5–7.5 and a dissolved oxygen probe is immersed in a non-flow through type of system.

15. A process as claimed in claim 1, wherein an external polarization voltage of −0.6 to −0.65 volts is applied to the system.

16. A process as claimed in claim 1, wherein the stability of the cell beads is checked by adding different glucose-glutamic acid (GGA) concentrations ranging from 30–300 mg/l and observing response, i.e. change in oxygen concentration in terms of change in current.

17. A process as claimed in claim 1, wherein the formulated cell beads are used for instant BOD estimation of different synthetic samples viz., glucose, glutamic acid, peptone and citric acid.

18. A process as claimed in claim 1, wherein the formulated cell beads are used to instantly sense the BOD load of a variety of industrial waste-waters having high-moderate-low biodegradability.

19. A process as claimed in claim 1, wherein a dissolved oxygen probe is used as a sensor to sense the dissolved oxygen content in the system in terms of current (nA).

* * * * *